(12) United States Patent
Paul

(10) Patent No.: US 11,446,521 B2
(45) Date of Patent: Sep. 20, 2022

(54) RADIATION THERAPY SYSTEM

(71) Applicant: Muir IP Ltd, Cork (IE)

(72) Inventor: Kevin Paul, Lisbon (PT)

(73) Assignee: Muir IP Ltd, Cork (IE)

( * ) Notice: Subject to any disclaimer, the term of this patent is extended or adjusted under 35 U.S.C. 154(b) by 43 days.

(21) Appl. No.: 16/757,563

(22) PCT Filed: Oct. 19, 2018

(86) PCT No.: PCT/EP2018/078772
§ 371 (c)(1),
(2) Date: Apr. 20, 2020

(87) PCT Pub. No.: WO2019/077135
PCT Pub. Date: Apr. 25, 2019

(65) Prior Publication Data
US 2020/0346040 A1 Nov. 5, 2020

(30) Foreign Application Priority Data

Oct. 20, 2017 (GB) ..................... 1717238

(51) Int. Cl.
*A61N 5/10* (2006.01)
*A61B 6/04* (2006.01)
*E04H 3/08* (2006.01)

(52) U.S. Cl.
CPC .......... *A61N 5/1067* (2013.01); *A61B 6/0407* (2013.01); *A61N 5/1048* (2013.01);
(Continued)

(58) Field of Classification Search
CPC .. A61N 5/1067; A61N 5/1048; A61N 5/1079; A61N 5/1082; A61N 2005/1087; A61B 6/0407; E04H 3/08
(Continued)

(56) References Cited

U.S. PATENT DOCUMENTS

| | | |
|---|---|---|
| 5,321,271 A | 6/1994 | Schonberg |
| 5,349,198 A | 9/1994 | Takanaka |

(Continued)

FOREIGN PATENT DOCUMENTS

| | | |
|---|---|---|
| EP | 986071 A2 | 3/2000 |
| EP | 3829709 A1 | 6/2021 |

(Continued)

OTHER PUBLICATIONS

International Search Report and Written Opinion of the ISA from corresponding PCT Application No. PCT/EP2018/078772, dated Jan. 22, 2019.

(Continued)

*Primary Examiner* — Nicole M Ippolito
(74) *Attorney, Agent, or Firm* — Gardner, Linn, Burkhart & Ondersma LLP

(57) ABSTRACT

A radiation therapy system comprises a beam delivery system located in a treatment room. The beam delivery system comprises a particle accelerator for generating a radiation beam, and a positioning apparatus for moving the particle accelerator to any one of a plurality of treatment locations in said treatment room. The system includes a plurality of waiting rooms each having a patient support apparatus that is movable between a waiting state in which it is located in the respective waiting room, and a treatment state in which it is located in a respective one of the treatment locations in the treatment room. The positioning apparatus comprises a counterbalanced lever which carries the particle accelerator. The particle accelerator is preferably a proton accelerator producing a proton beam.

19 Claims, 5 Drawing Sheets

(52) U.S. Cl.
CPC ......... *A61N 5/1079* (2013.01); *A61N 5/1082* (2013.01); *E04H 3/08* (2013.01); *A61N 2005/1087* (2013.01)

(58) Field of Classification Search
USPC ................. 250/492.1, 492.3; 600/1
See application file for complete search history.

(56) References Cited

U.S. PATENT DOCUMENTS

| | | | |
|---|---|---|---|
| 5,818,058 A | 10/1998 | Nakanishi | |
| 2006/0260050 A1 | 11/2006 | Manzione | |
| 2007/0131876 A1 | 6/2007 | Brahme | |
| 2011/0101254 A1 | 5/2011 | Yajima | |
| 2012/0241638 A1* | 9/2012 | Cao | A61B 6/4405 250/394 |
| 2013/0066134 A1* | 3/2013 | Carol | A61N 5/10 378/65 |
| 2013/0235969 A1 | 9/2013 | Winter et al. | |
| 2015/0087883 A1 | 3/2015 | Boudreau | |
| 2017/0189720 A1* | 7/2017 | Liu | A61B 6/102 |
| 2018/0014797 A1 | 1/2018 | Keibel | |

FOREIGN PATENT DOCUMENTS

| | | |
|---|---|---|
| WO | 9415670 A1 | 7/1994 |
| WO | 2008067893 A1 | 6/2008 |
| WO | 2013033249 A2 | 3/2013 |
| WO | 2014132502 A1 | 9/2014 |
| WO | 2015161036 A1 | 10/2015 |
| WO | 2019077135 A1 | 4/2019 |

OTHER PUBLICATIONS

UK Search Report of corresponding Application No. GB1717238.8, dated Mar. 26, 2018.
Commonly Assigned U.S. Appl. No. 17/604,486, filed Oct. 18, 2021.

* cited by examiner

RADIATION THERAPY SYSTEM

CROSS REFERENCE TO RELATED APPLICATION

The present applications claims the priority benefits of International Patent Application No. PCT/EP2018/078772, filed Oct. 19, 2018, and claims benefit of Great Britain Patent Application No. 1717238.8, filed Oct. 20, 2017.

FIELD OF THE INVENTION

The present invention relates to radiation therapy systems. The invention relates particularly, but not exclusively, to proton beam therapy systems.

BACKGROUND TO THE INVENTION

The NHS (National Health Service) in the United Kingdom and CRUK (Cancer Research UK) published a vision for future innovation in Radiotherapy 2014-2024 calling for improvements in cost, effectiveness, accessibility and technology for tumour-specific radiotherapy (RT).

Presently, RT is used to treat 40% of cancer patients, but current provision is hampered by lack of tumour specificity and toxicity, and the lack of a combined imagining modality that ensures tumours are properly targeted. Conventional X-rays are the current gold standard modality, but have inherent limitations in dose distribution. X-rays from medical linear accelerators (linacs) are the most common radiotherapy modality and are used in the treatment of 50% of cases. Although linac-based RT is cost-effective, it has disadvantages, including radiation-induced morbidity and carcinogenesis, which are largely caused by high entrance and distal doses in normal tissues. As linacs need to be replaced/upgraded every 10-20 years, they present a large financial burden to healthcare. Because X-ray radiotherapy is only partially effective and has side-effects, a key healthcare challenge is to find a more effective, less toxic and widely available modality so that patients receive appropriate and optimal care promptly, while meeting the increasing demand for radiotherapy.

Treatments using other charged particles, such as protons and ions, is known but are currently prohibitively expensive. The main cost drivers of proton and ion beam therapy are the proton and ion accelerators and beam delivery systems, which typically require very large gantries. The gantries themselves require high-tech engineering, with low production volume and are therefore expensive. The placement of the treatment rooms, which tend to be spread out over a large area also increases the overall cost. Single treatment room systems where the proton accelerator is placed on a gantry have also been proposed, but these are large systems requiring gantries and are relatively expensive because of the provision for only one treatment room. The foot print of the building is also influenced by the length of the beam line feeding the various treatment rooms and the required shielding along the beam line. In addition, with convention treatment systems it is difficult to make efficient use of the radiation equipment given the relatively long times required to set up the equipment for each patient and for organising the patients themselves.

Nevertheless it is understood that for the purpose of radiation therapy, protons provide a superior form of radiation compared to photons. For example, radiotherapy modalities such as proton and ion beam therapies are more effective because of their favourable dose distributions, where the "spread-out Bragg peak" can be made to conform to tumour shape with negligible distal dose, and there is a reduction in carcinogenesis arising from the treatment. Unfortunately the benefits of proton therapy have been overshadowed by the relatively high cost of conventional hospital based facilities.

By reducing the treatment cost of proton therapy the number of cancer patients receiving radiotherapy would increase. Making radiotherapy technology more affordable and widespread would improve the health and quality of life of cancer patients. The economy would also benefit through cost savings.

SUMMARY OF THE INVENTION

A first aspect of the invention provides a radiation therapy system comprising:
   a beam delivery system located in a treatment room, the beam delivery system comprising
      a particle accelerator for generating a radiation beam, and
      a positioning apparatus for moving said particle accelerator to any one of a plurality of treatment locations in said treatment room;
   a plurality of waiting rooms;
   a respective doorway between each waiting room and said treatment room;
   a respective patient support apparatus for each waiting room; and
   a respective actuation apparatus for moving each patient support apparatus between a waiting state in which it is located in the respective waiting room, and a treatment state in which it is located in a respective one of said treatment locations in said treatment room.

In preferred embodiments said positioning apparatus comprises a counterbalanced lever carrying the particle accelerator. Said lever may be pivotable at a fulcrum about a horizontal axis, said fulcrum preferably being located at the centre of said treatment room. Typically said particle accelerator is located on one side of said fulcrum and a counterbalancing unit is provided on the other side of the fulcrum.

In preferred embodiments, said positioning apparatus is rotatable about a vertical axis to move said particle accelerator to any one of said treatment locations, said vertical axis preferably being located at the centre of said treatment room.

Advantageously said fulcrum is coincident with said vertical axis.

Preferably the particle accelerator is coupled to the positioning apparatus for rotational movement about at least one axis, or two or three orthogonal axes, with respect to the positioning apparatus.

Advantageously said particle accelerator is provided with a beam output device, preferably comprising a beam delivery nozzle.

In preferred embodiments each of said treatment locations is a respective part of said treatment room associated with a respective one of said waiting rooms.

Typically each of said treatment locations is a respective part of said treatment room that is adjacent the door of a respective one of said waiting rooms.

In preferred embodiments at least some of, and preferably all of, said waiting rooms are radially spaced apart around said treatment room.

Preferably, said waiting rooms are arranged in a ring around said treatment room.

Preferably, said actuation apparatus is configured to move the respective patient support apparatus in a main axial direction into and out of the treatment room, said main axial direction preferably being radially disposed with respect to said treatment room. Optionally said actuation apparatus is configured to move the respective patient support apparatus along two or three orthogonal axes.

Optionally said actuation apparatus is configured to effect rotational movement of the patient support apparatus about at least one axis, and optionally about two or three orthogonal axes.

Conveniently said actuation apparatus comprises an articulated arm. The articulated arm may be coupled between a base and said patient support apparatus. The base is preferably located in the respective waiting room.

Preferably said actuation apparatus and/or said positioning apparatus are power operated.

In preferred embodiments the system includes a control system for controlling said beam delivery system for delivering a radiation beam to a target zone in accordance with a three dimensional beam delivery vector.

Preferably said control system is configured to control said beam delivery system by operating said positioning apparatus to position said particle accelerator for delivering said radiation beam to said target zone in accordance with said three dimensional beam delivery vector.

In preferred embodiments said control system is configured to control any one or more of: the rotational position of the positioning apparatus about a vertical axis; the height of the particle accelerator; the rotational position of the particle accelerator about one or more axis.

In preferred embodiments the system includes means for detecting movement of a patient on the patient support apparatus, the system being responsive to detected patient movement to adjust the position of said particle accelerator.

The control system may be responsive to detected patient movement to adjust said beam delivery system for maintaining delivery of said radiation beam to said target zone in accordance with said three dimensional beam delivery vector.

The system may include means for detecting movement of a patient on the patient support apparatus, the system being responsive to detected patient movement of more than a threshold amount to stop delivery of said radiation beam.

A second aspect of the invention provides a beam delivery system for a radiotherapy system, the beam delivery system comprising a particle accelerator for generating a radiation beam and a positioning apparatus for moving said particle accelerator, wherein said positioning apparatus comprises a counterbalanced lever carrying the particle accelerator. It will be understood that any one or more of the aforementioned features of the beam delivery system, particle accelerator and positioning apparatus may be provided with the beam delivery system of the second aspect of the invention.

Further advantageous aspects of the invention will be apparent to those ordinarily skilled in the art upon review of the following description of a specific embodiment and with reference to the accompanying drawings.

BRIEF DESCRIPTION OF THE DRAWINGS

An embodiment of the invention is now described with reference to the accompanying drawings in which.

DETAILED DESCRIPTION OF THE DRAWINGS

Figure 1:
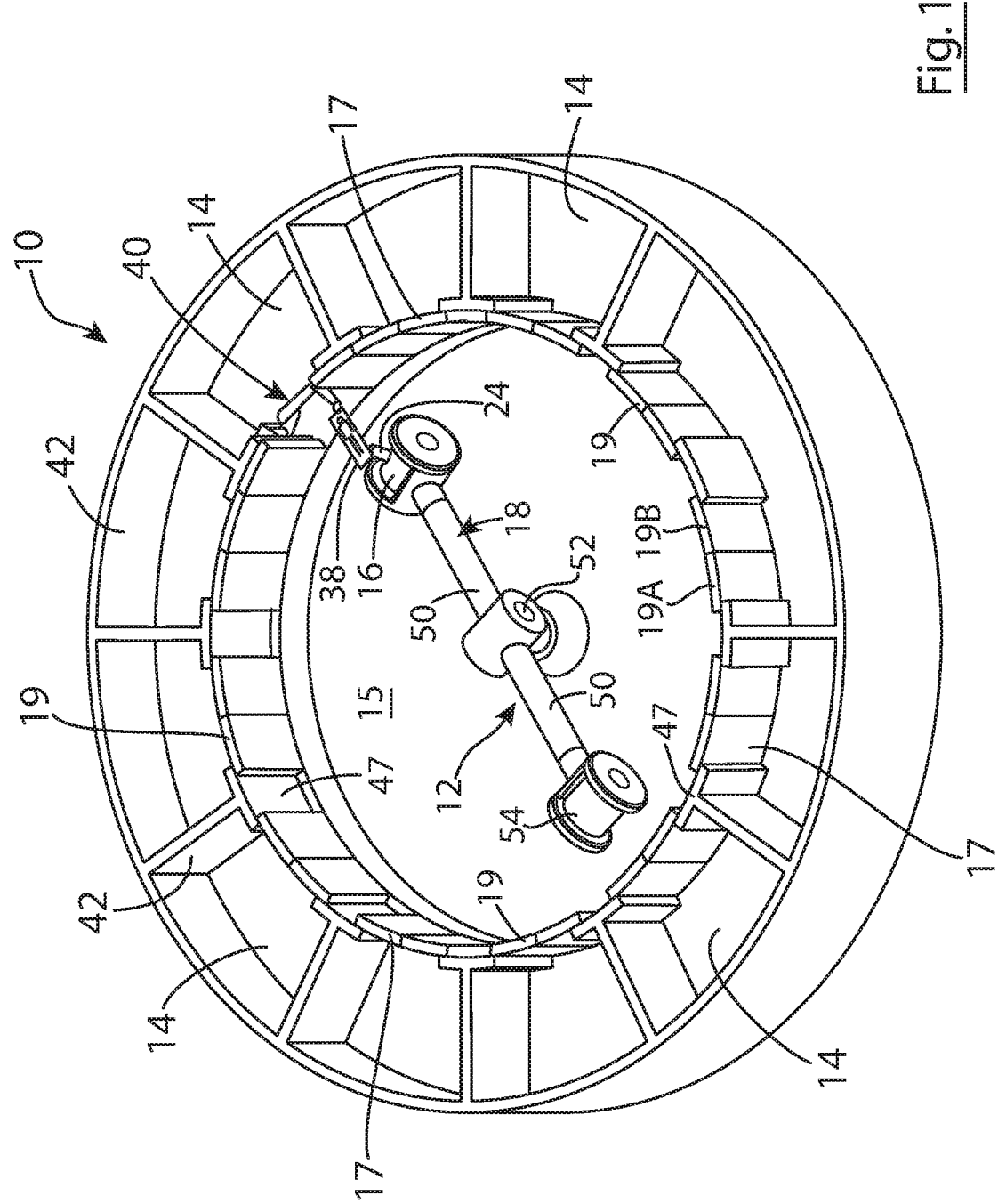
FIG. 1 is a perspective view of a radiation therapy system embodying one aspect of the present invention, the system being shown in a cut-away manner.
Figure 2:
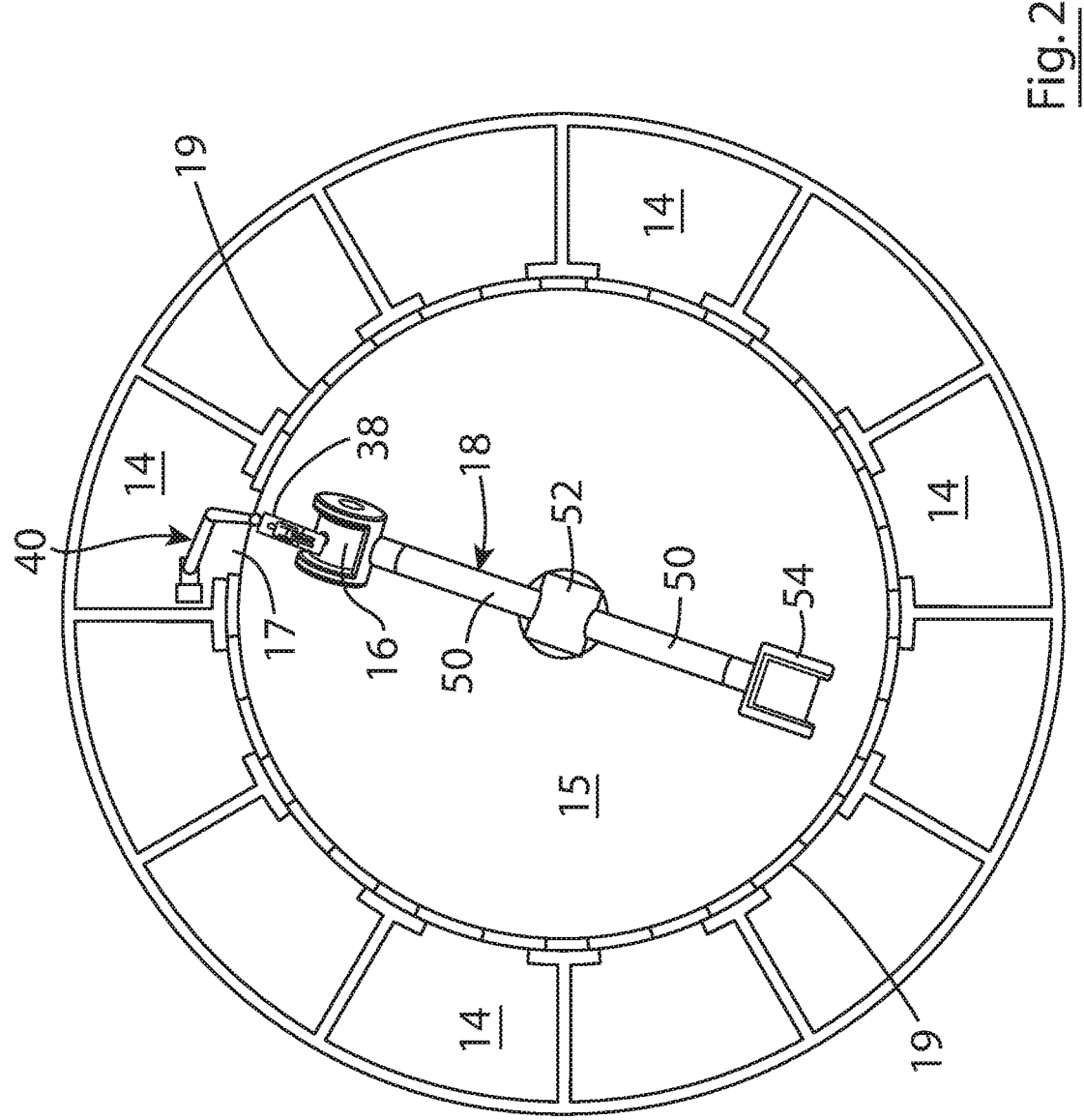
FIG. 2 is a plan view of the system of FIG. 1.
Figure 3:
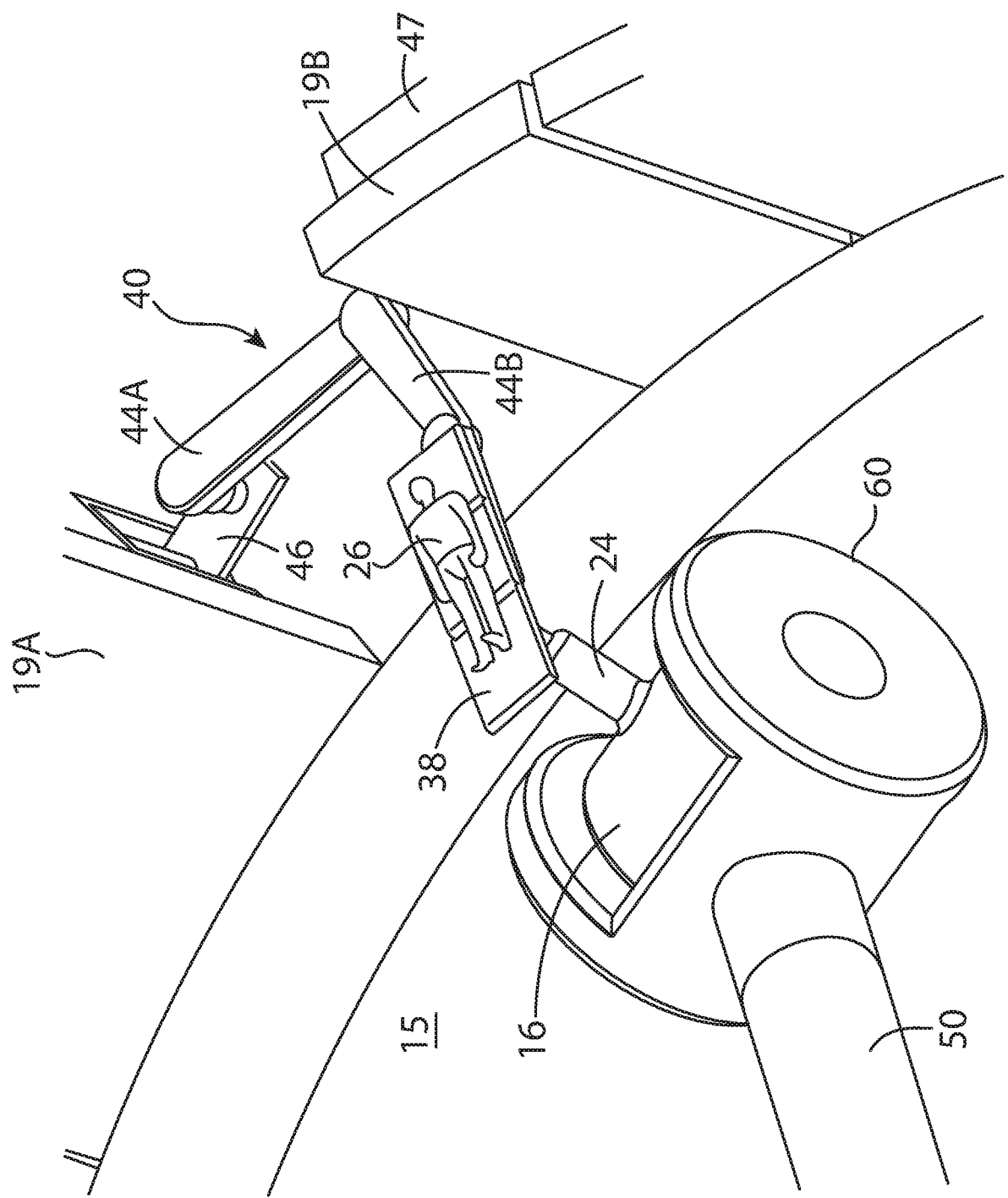
FIG. 3 is a perspective view of a patient being treated by the system of FIG. 1.
Figure 4:
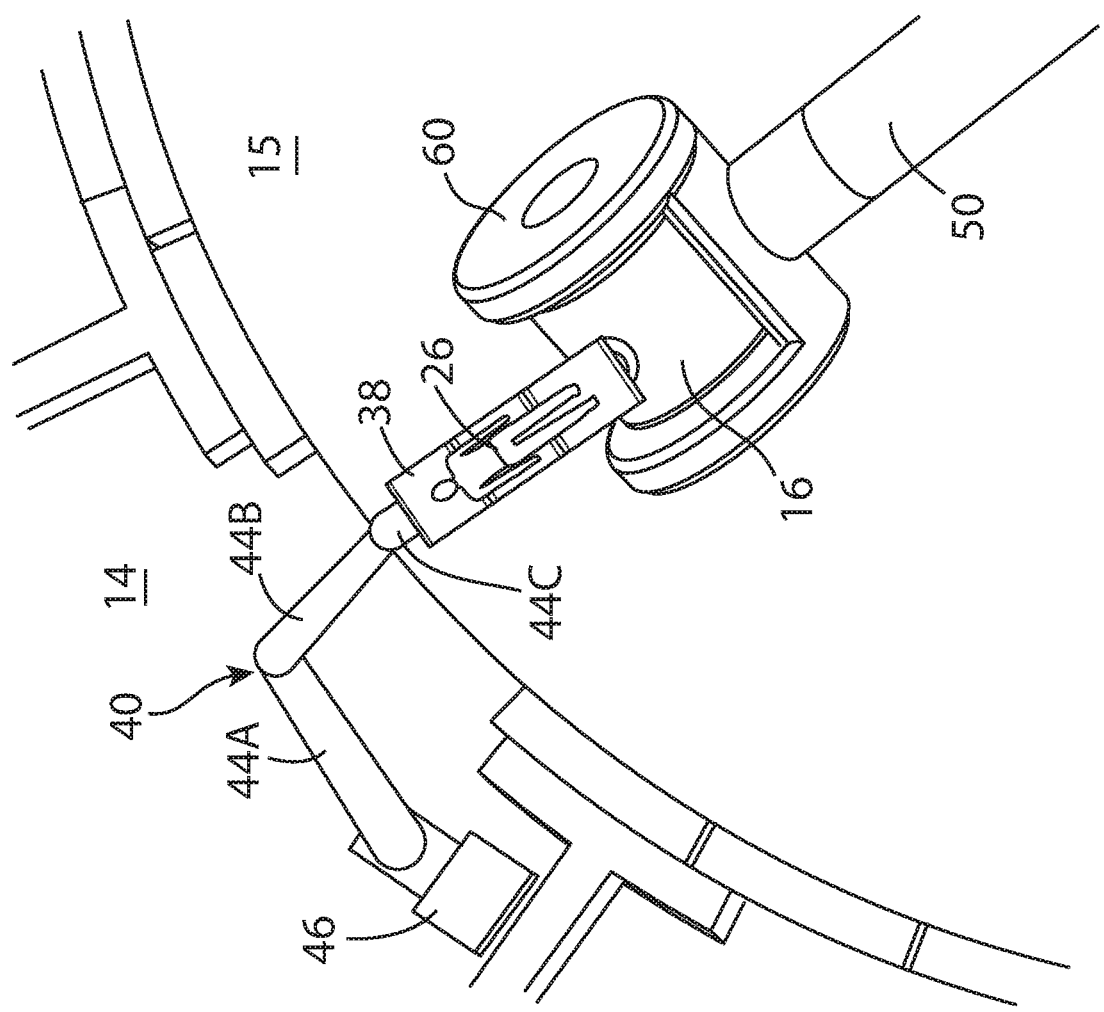
FIG. 4 is an alternative view of the patient being treated by the system.
Figure 5:
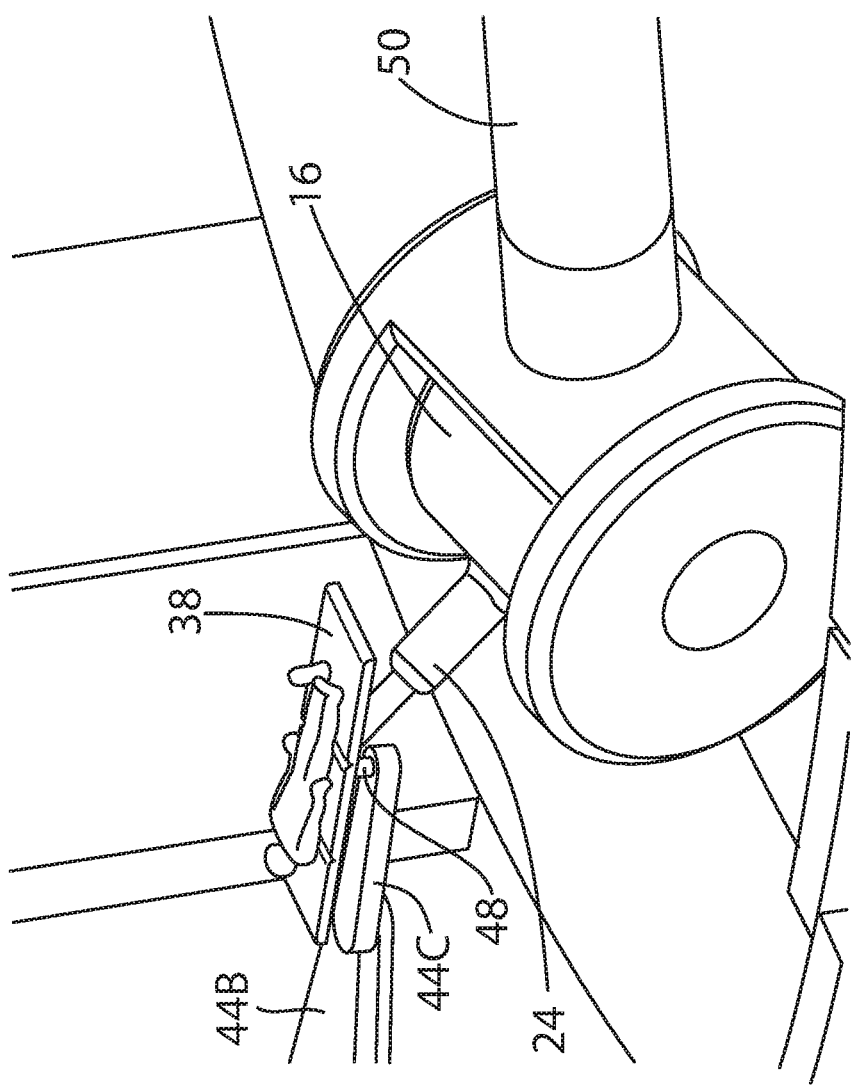
FIG. 5 is a further alternative view of the patient being treated by the system.

Referring now in particular to FIGS. 1 and 2 of the drawings there is shown, generally indicated as 10, a radiation therapy system embodying one aspect of the present invention. The system 10 includes a radiation beam delivery system 12 and a plurality of waiting rooms 14, the radiation beam delivery system 12 being operable to deliver a radiation beam to a patient 26 from any one of the rooms 14 at a time. In typical embodiments there is a single beam delivery system 12 servicing all of the rooms 14.

The beam delivery system 12 comprises a particle accelerator 16 carried by a positioning apparatus 18. The particle accelerator 16 may comprise any suitable conventional particle accelerator, for example a linear accelerator, a cyclotron, a synchro-cyclotron, a synchrotron, or a laser based accelerator, and produces a radiation beam (not illustrated) for use in patient treatments, in particular tumour RT. The radiation beam typically comprises ionizing radiation. The nature of the radiation beam depends on the radiation source (not shown) with which the particle accelerator 16 is used. In preferred embodiments, the radiation source comprises a source of protons. As such the radiation beam comprises a proton beam and the system 10 may be described as a proton therapy system. Alternatively, the radiation source may comprise other suitable particles, especially but not exclusively charged particles, for example ions (e.g. Carbon ions, Helium ions or Neon ions), atoms, photons or other sub-atomic particles such as electrons, alpha particles, beta particles, negative pi mesons or neutrons. Hence, in alternative embodiments the radiation beam may comprise, for example, an ion beam, electron beam (especially a relativistic electron beam), a neutron beam or X-ray beam. The radiation source may be incorporated into the particle accelerator 16 or connected to it in any convenient conventional manner.

The particle accelerator 16 has an output device, typically comprising a nozzle 24, for delivering the radiation beam to the radiation target, i.e. the patient 26 from the relevant waiting room 14. The nozzle 24 may be configured to bend, scan, focus or otherwise manipulate the radiation beam at the point of delivery, and to this end may include one or more bending, scanning and/or focusing magnets (and/or other beam forming and/or beam manipulating and/or energy selection components as required) for energy selection, bending, scanning and/or focusing the radiation beam at the point of delivery as required. Optionally, the nozzle 24 may be extendible in its longitudinal direction. The nozzle 24 may be conventional. Typically, the nozzle 24 is fixed with respect to the particle accelerator 16 so that it moves with the particle accelerator 16. In preferred embodiments there is no beam transport system between the particle accelerator 16 and the nozzle 24, in particular no beam transport system that bends the radiation beam between the particle accelerator 16 and the nozzle 24. This simplifies the beam delivery system 12, reducing cost and increasing reliability. It will be seen that in preferred embodiments, positioning the particle beam with respect to a patient involves moving the whole accelerator 16, and therefore the nozzle 24, by means of the positioning apparatus 18.

In preferred embodiments the beam delivery system 12 is located in a treatment room 15 that is adjacent each of the waiting rooms 14. Conveniently the waiting rooms 14 are radially spaced apart around the treatment room 15. In preferred embodiments, the rooms 14 are preferably arranged in a ring around the treatment room 15. The treatment room 15 may therefore be circular. Twelve waiting rooms 14 are shown in the illustrated example although in alternative embodiments there may be more or fewer waiting rooms. Although it is preferred that the waiting rooms 14 encircle the treatment room 15, this is not essential. In alternative embodiments, the waiting rooms 14 may be arranged in one or more arc formation located adjacent the treatment room 15 (in which case they may still be radially spaced apart), or may be arranged in one or more linear formation, i.e. in one or more row, located adjacent the treatment room 15. In such cases the waiting rooms 14 may only partially surround the treatment room 15. In cases where the waiting rooms 14 do form a ring surrounding the treatment room 15, the ring may be circular (as illustrated) or any other suitable shape, e.g. rectangular or polygonal. In the illustrated embodiment, the waiting rooms 14 are provided in a single tier. In alternative embodiments the waiting rooms 14 may be provided in more than one tier. Each tier may have the same arrangement of waiting rooms or a different arrangement of waiting rooms as is required.

A respective doorway 17 is provided between each waiting room 14 and the treatment room 15, each doorway 17 having a respective door 19. In the illustrated embodiment, each door 19 is a sliding door, comprising first and second slidable door leafs 19A, 19B. Alternatively, each door may comprises a single leaf, or more than two leafs, and may open and close in any convenient manner, e.g. slidably or hinged. Preferably, the doors 19 are configured to provide radiation shielding to the occupants of the respective room 14, e.g. the respective patient 26 and any medical staff that may be present. This may be achieved in any conventional manner, including selection of the material from which the structures are made and/or their thickness, and/or by providing appropriate cladding (not shown).

The walls 42, and optionally the floor and ceiling, of the rooms 14, 15 may be configured to provide radiation shielding to the room occupants. This may be achieved in any conventional manner, including selection of the material from which the structures are made and/or their thickness, and/or by providing appropriate cladding (not shown).

The treatment room 15 has a wall 47 that provides a barrier between the waiting rooms 14 and the treatment room 15. The doorways 17 are formed in the wall 47 and the respective doors 19, when closed, serve as part of the barrier.

Each waiting room 14 is associated with at least one patient support apparatus 38, typically in the form of a chair, couch, platform or bed, for accommodating the patent 26 during use. The support apparatus 38 provides at least one of, and may be operable between any two or more of the following configurations: a standing configuration (in which it supports the patent in a standing position), a sitting configuration (in which it supports the patient in a sitting position), a fully reclined configuration (in which it supports the patient in a fully reclined position), and one or more semi-reclined configurations.

Each patient support apparatus 38 is supported by an actuation apparatus 40 configured to move the patient support apparatus 38 between a waiting state, in which the patient support apparatus 38 is located in the respective waiting room 14, and a treatment state, in which the patient support apparatus 38 is located in the treatment room 15.

When the patient support apparatus 38 is moving between the waiting and treatment states, the respective door 19 is open to allow the patient support apparatus 38 to pass through the respective doorway 17. When the patient support apparatus 38 is in its waiting state, the respective door 19 is closed to isolate the respective waiting room 14 from the treatment room 15. In the illustrated embodiment, when the patient support apparatus 38 is in its treatment state, the respective door 19 is open to allow the actuation apparatus 40 to extend through the doorway 17. In alternative embodiments, for example where the base of the actuation apparatus 40 is located in the treatment room 15, the door 19 may be closed when the patient support apparatus 38 is in the treatment room 15.

The actuation apparatus 40 is configured to move the respective patient support apparatus 38 along at least one axis into and out of the treatment room 15. In preferred embodiments, the actuation apparatus 40 is configured to move the respective patient support apparatus 38 along a radial axis, i.e. in a direction that is along a radius of the treatment room 15. The axis is typically a horizontal axis. Optionally, the actuation apparatus 40 is configured to move the respective patient support apparatus 38 along one or more other axis, in particular two or three orthogonal axes, including horizontal and/or vertical axes, as desired. For example, in addition to the main axial movement into and out of the treatment room 15, the actuation apparatus 40 may be configured to move the patient support apparatus 38 up and down and/or from side to side (with respect to the main axial direction).

In preferred embodiments, the actuation apparatus 40 is configured to rotate, or pivot, the respective patient support apparatus 38 about at least one axis, including horizontal and/or vertical axes, and/or about two or three orthogonal axes.

In preferred embodiments therefore, the actuation apparatus 40 is configured to effect linear movement of the patient support apparatus 38 along at least one axis (for movement into and out of the treatment room 15) and optionally along two or more orthogonal axes, and optionally rotational movement of the patient support apparatus 38 about at least one axis, and optionally about two or more orthogonal axes.

The actuation apparatus 40 may be configured in any conventional manner in order to achieve the desired movability of the patient support apparatus 38. By way of example, in the illustrated embodiment the actuation apparatus 40 comprises an articulated arm 44. In this example the arm 44 comprises three arm sections 44A, 44B, 44C pivotably coupled to each other in series, each section being coupled to the, or each, adjacent section for pivoting movement about a respective, in use, vertical axis. In alternative embodiments, the arm 44 may have more or fewer arm sections. The first arm section 44A is pivotably coupled to a base 46 for pivoting movement about a respective, in use, vertical axis. The base 46 is located in the respective waiting room 14 in this example, although it may alternatively be located elsewhere, e.g. in the treatment room 15. The coupling between the first arm section 44A and the base 46 may be configured to raise and lower the arm 44.

The last arm section 44C is coupled to the patient support apparatus 38. In this example the coupling between the arm 44 and the patient support apparatus 38 allows rotational movement of the patient support apparatus 38 about an, in use, vertical axis (or an axis that is perpendicular to the arm 44). In alternative embodiments, the coupling 48 between the arm 44 and the patient support apparatus 38, which may take any convenient conventional form, may be configured to allow additional or alternative movement of the patient support apparatus 38 with respect to the arm 44. In particular, any of the aforementioned rotational movement may be effected by the coupling 48 and/or linear movement in a vertical direction. In cases where the patient support apparatus 38 has more than one configuration, the coupling 48 may provide all or part of the means for operating the patient support apparatus 38 between its respective configurations.

Typically, the actuation apparatus 40 is power operated, e.g. by one or more power operated actuators (not shown), which may for example be electrically or hydraulically operated as is convenient, and may be linear or rotary as required.

In the drawings, the patient support apparatus 38 and associated actuation apparatus 40 are only shown in one of the waiting rooms 14 although it will be understood that each of the waiting rooms 14 is equipped in the same or similar manner. Hence, the system 10 can accommodate multiple patients at once, one per room 14.

It will be apparent from the foregoing that, in either of the waiting or treatment states, the patient support apparatus 38 may adopt any one of a plurality of different positions and/or orientations. However, in the waiting state (not illustrated) the patient support apparatus 38 is located in the respective waiting room 14, while in the treatment state it is located in the treatment room 15.

When in its treatment state, each patient support apparatus 38 occupies a respective different part of the treatment room 15, typically a part that is adjacent the respective doorway 17 of the respective waiting room 14, or which otherwise corresponds with the respective waiting room 14, typically in the vicinity of the wall 47. These respective parts of the treatment room 15 are spaced apart, usually around or along the wall 47 or otherwise around or along the periphery of the treatment room 15. For example in the illustrated embodiment, these respective parts of the treatment room 15 are radially spaced apart.

Accordingly, in order to treat patients from each waiting room 14, at least part of the beam delivery system 12 is movable so that it may deliver a radiation beam to any one of these parts of the treatment room 15. In preferred embodiments, the positioning apparatus 18 is operable to move the particle accelerator 16 within the treatment room 15 so that it may deliver the radiation beam to any one of said parts of the treatment room 15. Typically this involves moving the particle accelerator 16 to the respective part of the treatment room 15.

In preferred embodiments, the positioning apparatus 18 is configured to move the particle accelerator 16 to any one of the treatment parts of the treatment room 15, each treatment part being associated with a respective one of the waiting rooms 14. The preferred positioning apparatus 18 comprises a counterbalanced lever 50 that carries the particle accelerator 16 on one side of a pivot or fulcrum 52, and a counterbalancing unit 54 on the other side of the fulcrum 52. The fulcrum 52 in this case allows the lever 50 to pivot about an, in use, horizontal axis. The counterbalancing unit 54 may take any suitable form, e.g. comprising any object(s) having a mass that counterbalances the particle accelerator 16. Optionally, the counterbalancing unit 54 may comprise a second particle accelerator, which may be the same as or similar to the particle accelerator 16. This allows a second patient (not shown) from a second waiting room 14 to be treated simultaneously with the first patient 26 but in different, typically opposite, parts of the treatment room 15.

In the illustrated embodiment, the lever 50 comprises an arm but may alternatively comprise any other structure that is capable of carrying the particle accelerator 16 and counterbalancing unit 54. The lever 50 is typically of fixed length between the pivot point 52 and the particle accelerator 16, but may alternatively be extendible in length. The lever 50 may be of fixed length between the pivot point 52 and the counterbalancing unit 54, but may alternatively be extendible in length. In preferred embodiments, the fulcrum 52 is located at the centre of the treatment room 15 and the length of the lever 50 between the fulcrum 52 and the particle accelerator 16 is such that the particle accelerator 16 is locatable at any one of the treatment parts of the treatment room 15.

In preferred embodiments, the lever 50 is rotatable about a vertical axis, i.e. in the floor-to-ceiling direction of the treatment room 15, at the fulcrum 52. Hence, the particle accelerator 16 can be moved from one treatment part of the treatment room 15 to another treatment part by rotating the lever 50 about the vertical axis. Typically this involves rotating the lever 50 to align the particle accelerator 16 with any selected one of the waiting rooms 14, usually with the respective doorway 17 of the selected waiting room 14. The arrangement is such that when the patient support apparatus 38 of the respective waiting room 14 is in its treatment state, the particle accelerator 16 is in a position to deliver the radiation beam to the patient 26. Any conventional support mechanism(s) may be used at the fulcrum 52 to enable the desired pivoting and rotational movement of the lever 50.

Accordingly, in preferred embodiments, the positioning apparatus 18 is able to raise and lower the particle accelerator 16 (in this case by pivoting the lever 50 about a horizontal axis at the fulcrum 52), and move the particle accelerator 16 from one part of the treatment room 15 to another (in this case by rotating the lever 50 about the vertical axis at the fulcrum 52), advantageously with the assistance of the counterbalancing provided by the counterbalancing unit 54.

In the drawings, the nozzle 24 is shown in a location from where it can deliver the radiation beam to the patient from beneath the patient support apparatus 38. It will be understood that this is exemplary and that the beam delivery system may alternatively be configured such that the nozzle 24 targets the patient from above, or from either side, from the front or the rear of the patient support apparatus 38.

In alternative embodiments, the particle accelerator 16 may be carried by an arm, or other structure, that is capable of being rotated about a vertical axis as described above but which is not part of a counterbalanced lever. Such an arrangement allows the particle accelerator 16 to be moved from one treatment part of the treatment room 15 to another, but the lack of a counterbalance makes the particle accelerator 16 difficult to manoeuvre.

In preferred embodiments, the particle accelerator 16 is carried by a head unit 60 of the positioning apparatus 18, which is conveniently provided at the free end of the lever 50. Advantageously the particle accelerator 16 is rotatable with respect to the head unit 60 about an axis that is perpendicular to the longitudinal axis of the lever 50. The head unit 60 may be rotatable with respect to the lever 50 about an axis that is parallel with the longitudinal axis of the lever 50. More generally, the particle accelerator 16 may be coupled to the positioning apparatus 18 for rotational movement about at least one axis, or two or three orthogonal axes, with respect to a supporting structure such as the arm 56 or lever 50.

In alternative embodiments (not illustrated) the nozzle 24 may be connected to the particle accelerator 16 by a beam transport system configured to allow the radiation beam to be delivered to any one of said parts of the treatment room 15. For example the beam transport system may provide a respective beam transport path to each part of the treatment room 15, or may support movement of the nozzle 24 from one location to another. The beam transport system may be conventional in design, typically including one or more vacuum tubes, and components (e.g. magnets) for beam bending, beam focusing and/or energy selection).

Optionally, the positioning apparatus 18, or more generally the beam delivery system 12, is mounted on a platform (not shown) or other lifting structure that is movable in a vertical direction, i.e. in the floor-to-ceiling direction of the treatment room 15, in order to raise and lower the positioning apparatus 18/beam delivery system 12. This is particularly useful in cases where the beam delivery system 12 is required to service waiting rooms 14 arranged in more than one tier.

Preferably, the positioning apparatus 18 is power operated, e.g. by one or more power operated actuators (now shown), which may for example be electrically or hydraulically operated as is convenient, and may be linear or rotary as required.

During use, the positioning apparatus 18 moves the particle accelerator 16 to any one of a plurality of treatment locations within the treatment room 15, each treatment location being a respective part of the treatment room 15 that is associated with a respective one of the waiting rooms 14. In preferred embodiments, this is achieved by rotating the positioning apparatus 18, and more particularly lever 50, about a vertical axis to locate the particle accelerator 16 in any one of the treatment locations as determined by the rotational position of the lever 50. When the particle accelerator 16 is at the treatment location for a given waiting room 14 (the treatment location typically being adjacent the doorway 17 of the respective room 14), and the patient support apparatus 38 of the respective room 14 is in its treatment state, the beam delivery system 12 can be operated to deliver the radiation beam to the patient 26 on the support apparatus 38. After treatment is completed, the positioning apparatus 18 may move the particle accelerator 16 to another one of the treatment locations in order to treat a patient from another of the waiting rooms 14. Accordingly, the particle accelerator 16 is moved within the treatment room 15 from one treatment location to another in order to treat patients from any one or more of the waiting rooms 14, one patient at a time. Hence the beam delivery system 12 is shared by multiple waiting rooms 14. For example, the therapy system 10 may be operated to deliver a radiation beam to treatment locations associated with two or more of the waiting rooms 14 in succession, conveniently in a progressive angular direction around the ring of rooms 14, in order to treat a respective patient 26 from each room.

Preferably, the door 19 of each waiting room 14 that is not at any given time being serviced by the beam delivery system 12, is closed.

Systems 10 embodying the invention typically include a control system (not shown), which may be located in a separate room. The control system may include equipment for controlling and monitoring any aspect of the system 10 and may take any suitable conventional form, typically including suitable programmed computing device(s). The control system typically includes means for controlling and/or monitoring the operation of any one or more of the accelerator 16 (including the nozzle 24), positioning apparatus 18, the actuation apparatus 40, the patient support apparatus 38 and the doors 19 as applicable. The control system may include components (e.g. scanner(s), visual display unit(s) and user interface device(s)) of an imaging system for controlling and/or monitoring operation of the system 10. The imaging system may comprise any one or more of an MRI system, PET system, SPECT system or CT system. The control system may be configured to control any one or more components of the system 10 collectively or individually.

Preferred embodiments of the invention provide a low redundancy, centralised, therapy system with highly configurable (i.e. can be placed at any position in space and be rotated in all planes i.e. 6D $(x,y,z,\theta,\phi)$ radiation delivery.

Preferred embodiments include a centralised beam delivery system 12, which may produce radiation from single or multiple radiation sources (to provide redundancy for maintenance, which is optional), that can be arbitrarily positioned in up to three dimensions and pointed in any direction such that the emitted radiation beam can be targeted on a patient from any one of a plurality of waiting rooms at a range of angles.

Each waiting room 14 advantageously has a patient support apparatus 38 that can be positioned in up to 6 cartesian dimensions $(x,y,z,\theta,\phi,\Psi)$, optionally with additional reclining adjustments, and optionally with different support heights, and/or different positions and angles with respect to the room. The preferred patient support apparatus 38 is adjustable to move the patient along one axis, or in two or three orthogonal axial directions (a vertical axis and two perpendicular horizontal axes).

Advantageously, the patient support apparatus is adjustable to pivot the patient about at least one, or two or three orthogonal axes (a vertical axis and two perpendicular horizontal axes). This facilitates a wide range of relative angles and positions of the delivered radiation beam relative to the patient support apparatus.

Advantageously, the adjustability of the patient support apparatus 38 (as facilitated at least in part by the actuation apparatus 40) and/or of the beam delivery system 12 (as facilitated by the positioning apparatus 18 and the accelerator 16) individually or together allow the radiation beam to be delivered in a precise and highly adjustable manner (advantageously in up to 6 cartesian dimensions $(x,y,z,\theta,\phi,\Psi)$) to a target zone in any one of the treatment locations of the treatment room 15. In particular the radiation beam may be targeted at the target zone 3 dimensionally.

Advantageously, the adjustability of the beam delivery system 12 is configured to provide isocentric delivery of the radiation beam to a target zone in any one of the treatment locations in the treatment room 15 (which target zone coincides in use with a patient on the relevant patient support apparatus 38). Advantageously, the system 10 allows substantially full 3-D Isocentric irradiation of a patient, suitable for intensity modulated therapy or spot scanning.

Scanning of the radiation beam about at least one and preferably two perpendicular axes (e.g. a vertical axis and a perpendicular horizontal axis running transversely of the room) may be supported, conveniently by incorporation of scanning magnets in the nozzle 24.

Advantageously, during use the relative positions and angles of the system 10 may be adjusted to achieve isocentric irradiation of the target zone.

The use of a counterbalanced positioning apparatus is advantageous in that it allows the particle accelerator 16 to be moved in the manner described, which would be beyond the capability of conventional robots since particle accelerators can weight between 100-200 tonnes and so are conventionally deployed statically.

Providing the nozzle 24 at the particle accelerator 16 without an intermediate beam transport system is advantageous since it avoids or reduces beam degradation and collateral residual radiation that can be caused by bending magnets and other components of a beam transport system. Moreover, as there is no long beam line or 2D gantry, the maintenance, energy requirements, size, scale and costs of the system are reduced in comparison with conventional systems.

During use, the control system obtains treatment information in respect of the next waiting room 14 to be serviced. The treatment information typically includes beam delivery vector(s) for targeting the beam on a target zone, and dosage information. The control system then causes the positioning apparatus 18 to position the particle accelerator 16 at the relevant treatment location in the room 15, as well as positioning the nozzle 24 in a desired position and/or orientation as determined from the treatment information, i.e. in order to deliver the radiation beam at the required delivery vector(s).

3D targeting of the radiation beam may be performed by a laser so that the radiation beam always impinges on the target zone as desired.

In preferred embodiments, the control system includes one or more devices (e.g. cameras and/or motion sensors and/or pressure sensors) for detecting movement of the patient when on the patient support apparatus 38. The control system may be configured to use any detected movement of the patient to re-position one or more component of the system 10, in particular of the beam delivery system 12, to ensure that the radiation beam is correctly targeted on the patient, i.e. the delivery of the beam automatically tracks any detected movement of the patient during use. Optionally, if any detected movement exceeds a threshold level, then the control system may be configured to cease treatment.

The invention is not limited to the embodiment(s) described herein but can be amended or modified without departing from the scope of the present invention.

The invention claimed is:

1. A radiation therapy system comprising:
a beam delivery system located in a treatment room, the beam delivery system comprising
a particle accelerator for generating a radiation beam, and
a positioning apparatus for moving said particle accelerator to any one of a plurality of treatment locations in said treatment room;
a plurality of waiting rooms;
a respective doorway between each waiting room and said treatment room;
a respective patient support apparatus for each waiting room; and
a respective actuation apparatus for moving each patient support apparatus between a waiting state in which it is located in the respective waiting room, and a treatment state in which it is located in a respective one of said treatment locations in said treatment room.

2. The system of claim 1, wherein said positioning apparatus comprises a counterbalanced lever carrying the particle accelerator.

3. The system of claim 2, wherein said lever is pivotable at a fulcrum about a horizontal axis, said fulcrum preferably being located at the centre of said treatment room.

4. The system of claim 3, wherein said particle accelerator is located on one side of said fulcrum and a counterbalancing unit is provided on the other side of the fulcrum.

5. The system of claim 1, wherein said positioning apparatus is rotatable about a vertical axis to move said particle accelerator to any one of said treatment locations, said vertical axis preferably being located at the centre of said treatment room.

6. The system of claim 1, wherein the particle accelerator is coupled to the positioning apparatus for rotational movement about at least one axis, or two or three orthogonal axes, with respect to the positioning apparatus.

7. The system of claim 1, wherein said particle accelerator is provided with a beam output device, preferably comprising a beam delivery nozzle, and wherein there is no beam transport system between the particle accelerator and the beam output device.

8. The system of claim 7, wherein the beam output device is fixed with respect to the particle accelerator so that it moves with the particle accelerator.

9. The system of claim 1, wherein each of said treatment locations is a respective part of said treatment room associated with a respective one of said waiting rooms, being adjacent a door of a respective one of said waiting rooms.

10. The system of claim 1, wherein at least some of, and preferably all of, said waiting rooms are radially spaced apart around said treatment room, said waiting rooms being arranged in a ring around said treatment room.

11. The system of claim 1, wherein said actuation apparatus is configured to move the respective patient support apparatus in a main axial direction into and out of the treatment room, said main axial direction preferably being radially disposed with respect to said treatment room, said actuation apparatus being configured to move the respective patient support apparatus along two or three orthogonal axes and/or to effect rotational movement of the patient support apparatus about at least one axis, and optionally about two or three orthogonal axes.

12. The system of claim 1, wherein said actuation apparatus comprises an articulated arm coupled between a base and said patient support apparatus.

13. The system of claim 12, wherein said base is located in the respective waiting room.

14. The system of claim 1, wherein said actuation apparatus and/or said positioning apparatus are power operated.

15. The system of claim 1, further including a control system for controlling said beam delivery system for delivering a radiation beam to a target zone in accordance with a three dimensional beam delivery vector, and wherein said control system is configured to control any one or more of: the rotational position of the positioning apparatus about a vertical axis; the height of the particle accelerator; the rotational position of the particle accelerator about one or more axis.

16. The system of claim 1, wherein said control system is configured to control said beam delivery system by operating said positioning apparatus to position said particle accelerator for delivering said radiation beam to said target zone in accordance with said three dimensional beam delivery vector.

17. The system of claim 1, further including means for detecting movement of a patient on the patient support apparatus, the system being responsive to detected patient movement to adjust the position of said particle accelerator, and/or being responsive to detected patient movement of more than a threshold amount to stop delivery of said radiation beam.

18. The system of claim 15, wherein said control system is responsive to detected patient movement to adjust said beam delivery system for maintaining delivery of said radiation beam to said target zone in accordance with said three dimensional beam delivery vector.

19. The system of claim 1, wherein said particle accelerator is a proton accelerator and said radiation beam is a proton beam.

\* \* \* \* \*